(12) United States Patent
Schultes

(10) Patent No.: US 11,317,808 B2
(45) Date of Patent: May 3, 2022

(54) OPTICAL MARKER TO ADJUST THE TURNTABLE OF A 3D BODY SCANNER

(71) Applicant: Naked Labs Austria GMBH, Vienna (AT)

(72) Inventor: Gerhard Schultes, Premstaetten (AT)

(73) Assignee: Naked Labs Austria GMBH, Vienna (AT)

( * ) Notice: Subject to any disclaimer, the term of this patent is extended or adjusted under 35 U.S.C. 154(b) by 557 days.

(21) Appl. No.: 16/316,941

(22) PCT Filed: Jul. 13, 2017

(86) PCT No.: PCT/EP2017/067669
§ 371 (c)(1),
(2) Date: Jan. 10, 2019

(87) PCT Pub. No.: WO2018/011334
PCT Pub. Date: Jan. 18, 2018

(65) Prior Publication Data
US 2019/0239748 A1 Aug. 8, 2019

(30) Foreign Application Priority Data
Jul. 13, 2016 (DE) .................... 10 2016 112 901.1

(51) Int. Cl.
*A61B 5/00* (2006.01)
*A61B 5/107* (2006.01)

(52) U.S. Cl.
CPC .......... *A61B 5/0064* (2013.01); *A61B 5/1079* (2013.01); *A61B 5/706* (2013.01); *A61B 5/6891* (2013.01)

(58) Field of Classification Search
CPC combination set(s) only.
See application file for complete search history.

(56) References Cited

U.S. PATENT DOCUMENTS

| 2002/0085219 | A1* | 7/2002 | Ramamoorthy | ....... H04N 19/46 |
| | | | | 358/1.9 |
| 2007/0021940 | A1 | 1/2007 | Peter et al. | |
| 2008/0245972 | A1* | 10/2008 | Drapeau | ............... A61B 5/0064 |
| | | | | 250/475.2 |
| 2011/0251478 | A1* | 10/2011 | Wieczorek | ........... A61B 5/1127 |
| | | | | 600/411 |
| 2012/0110739 | A1* | 5/2012 | Rawls-Meehan | .... A47C 20/041 |
| | | | | 5/616 |
| 2013/0286012 | A1* | 10/2013 | Medioni | ................... G06T 7/00 |
| | | | | 345/420 |

(Continued)

OTHER PUBLICATIONS

International Preliminary Report on Patentability, PCT/EP2017/067669, dated Jan. 24, 2019, 2 pages.

(Continued)

*Primary Examiner* — Yi-Shan Yang
(74) *Attorney, Agent, or Firm* — Dority & Manning, P.A.

(57) ABSTRACT

A 3D body scanner for generating a 3-D body model includes a turntable configured and disposed for carrying a body that is to be scanned. The 3D body scanner includes a light emitter that is configured and disposed for projecting an optical marker indicating where the turntable should be situated in relation to the 3D body scanner. The 3D body scanner includes a diffuser, a feedback device and a wireless interface.

9 Claims, 2 Drawing Sheets

(56) References Cited

U.S. PATENT DOCUMENTS

| | | | | |
|---|---|---|---|---|
| 2015/0313566 A1* | 11/2015 | Diers | ................... | A61B 6/5217 |
| | | | | 378/63 |
| 2016/0140717 A1 | 5/2016 | Ohira et al. | | |
| 2017/0000675 A1* | 1/2017 | Hight | ................... | A61B 6/0492 |
| 2017/0211930 A1* | 7/2017 | Lee | ........................ | G01B 11/24 |
| 2018/0299554 A1* | 10/2018 | Van Dyck | ............... | G01S 17/18 |

OTHER PUBLICATIONS

Written Opinion of the International Searching Authority, PCT/EP2017/067669, dated Jan. 24, 2019, 5 pages.
International Search Report, PCT/EP2017/067669, dated Oct. 26, 2017, 14 pages.
Naked Labs Unveils World's First 3D Fitness Tracker, https://www.prnewswire.com/news-releases/naked-labs-unveils-worlds-first-3d-fitness-tracker-300251292.html, Jul. 27, 2017, 5 Pages.

* cited by examiner

OPTICAL MARKER TO ADJUST THE TURNTABLE OF A 3D BODY SCANNER

CROSS-REFERENCE TO RELATED APPLICATIONS

The present application is related by subject matter to the following concurrently filed PCT applications (all of which designate the US):

a. International Application No.: PCT/EP2017/067668; entitled "Determination of Body Fat Content by Body-Volume-Distribution and Body-Impedance-Measurement".

b. International Application No.: PCT/EP2017/067669; entitled "Optical Marker to Adjust the Turntable of a 3D Body Scanner," which claims priority to German Application No.: DE10 2016 112 901.1.

c. International Application No.: PCT/EP2017/067761; entitled "Efficient Volumetric Reconstruction with Depth Sensors".

d. International Application No.: PCT/2017/067672; entitled "Skeleton Estimation from Body Mesh".

e. International Application No.: PCT/2017/067667; entitled "Method for Creating a 3D-Model and 3D-Body-Scanner".

f. International Application No.: PCT/2017/067664; entitled "Smart Body Analyzer with 3D Body Scanner and Vital Parameter Sensors".

g. International Application No.: PCT/EP2017/067665; entitled "Motor Driven Turntable with Foldable Sensor Mast," which claims priority to German Application No.: DE 10 2016 112 893.7.

h. International Application No.: PCT/EP2017/067671; entitled "Alignment of Scan Parts on a Turntable," which claims priority to German Application No.: DE 10 2016 112 890.2.

The above cited PCT international applications are hereby incorporated herein in their entireties by this reference for all purposes. Any combination of the features and aspects of the subject matter described in at least one of the incorporated applications may be combined with embodiments of the present application to yield still further embodiments of the present invention.

FIELD OF THE INVENTION

The invention relates to a 3D body scanner for generating a 3D body model, wherein the 3D body scanner comprises a turntable as a first part for turning around a body to be scanned and a separate second part for scanning the body. The 3D body scanner is suitable for at least one of fitness monitoring, personal biofeedback and medical diagnostic apparatus.

BACKGROUND OF THE INVENTION

From the GB 2504711 B, an apparatus for generating a 3D representation of a subject such as a person is known. The apparatus comprises a display such as a television set. A RGB-D sensor is mounted on the display. The RGB-D sensor is capable of generating a RGB image and a depth image of the scene in front of the display. An area of available space is located on the floor in front of the display. The display is configured to display indications to guide a subject to the area of available space. Once the subject is standing in the correct location, the display is configured to display indications to guide the subject to a pose. The foot location is rendered using Augmented-Reality that is superimposed with the RGB image. The foot location is rendered as a circle on the ground plane enclosing two rendered shoes.

Today accurate 3D human body models are demanded by various fields of applications:

Fitness and body styling application,
Medical applications,
Cloth manufacturing industry,
Cloth internet and retail shops and/or
Automotive industry.

To generate such a 3D model of the human body, a 3D scanner is used. 3D body scanners generally use (whatever type of) Depth Sensors to determine the three dimensions of the body (object). Therefore the body has to be seen by the Depth Sensors from multiple positions to obtain the full set of information to generate the 3D body model. Nowadays 3D scanners work according to these three principles:

Rotating the body (object),
Rotating or shifting the depth sensors,
Multiple Steady-State Depth Sensors or
Combination of Concepts.

Rotating the Body (Object):

The body is in an as far as possible steady state pose when rotated by a turntable to give the Depth Sensors visibility to all sides of the body. To ensure a correct and optimum performance scan, the rotating element (turntable) has to be placed in a correct geometrical location (distance, angle) with respect to the depth sensors. This is ensured either by:

1. a mechanical setup of the scanner in one part or
2. the parts of the scanner containing the depth sensors on one hand and the parts of the scanner carrying and rotating the body (object) on the other hand have to be placed in a defined distance and angle with respect to one another as given in the user's manual, maybe using a mechanical template.

Rotating or Shifting Depth Sensors:

The body is in an as far as possible steady state pose and the Depth Sensors are rotated around the body to give them visibility to all sides of the body. The object (body) needs to be placed in a certain optimum position inside the scanner, thus ensuring best visibility by the depth sensors. This disposition is typically ensured by colored footprints or similar on the carrier of the body (object).

Multiple Steady-State Depth Sensors:

The body is in an as far as possible steady state pose and Depth Sensors are placed in two or more positions around the body to give the 3D scanner visibility to all sides of the body. To ensure a correct and optimum performance scan, multiple fixed elements of the 3D scanner have to be placed in a correct geometrical location (correct mutual distance pattern and angle of view) with respect to the depth sensors. This is ensured for example either by:

1. a large and heavy mechanical setup of the scanner in one part or
2. using a removable base frame or some other kind of removable mechanical template for placement of the pillars containing the depth sensors.

Combination of Concepts:

Combined concepts typically (i) turn around the body (object) and (ii) move one depth sensor in height instead of using multiple depth sensors at different constant heights.

To ensure a correct and optimum performance scan, the rotating element (turntable) has to be placed in a correct geometrical location (distance, angle) with respect to the depth sensors. This is ensured either by:
1. a mechanical setup of the scanner in one part or
2. the parts of the scanner containing the depth sensors on one hand and carrying and rotating the body (object) on the other hand have to be placed in a defined distance and angle with respect to one another as given in the user's manual, maybe using a mechanical template.

At setup of such 3D body scanners these geometrical relations have to be fulfilled in an accurate way.

This is easy to achieve if the 3D body scanner is composed of some mechanically well interlinked parts which ensure these geometrical relations. Unfortunately, this requires the availability of enough space for accommodating heavy and expensive constructions.

Alternative constructions split the 3D body scanner into two or more independent parts which have to be placed in an accurate way before a 3D scan is made.

A setup using measuring tape and protractor is time consuming and not reasonable to the average skilled user. An alternative is the use of templates but these are large and unwieldy in use.

BRIEF OBJECTS AND SUMMARY OF THE INVENTION

The object of the present invention is to provide a 3D body scanner, in particular for generating a 3D body model that is designed such that a turntable and a separate second part can, in particular frequently, be adjusted to each other easy and fast.

The aforementioned object is achieved by means of a 3D body scanner for generating a 3D body exhibiting the features disclosed in the following description.

Proposed is a 3D body scanner, in particular for generating a 3D body model, which comprises a turntable as a first part for turning around a body to be scanned and at least one second part for scanning the body. The turntable is separated from the second part. The second part comprises at least one light emitter for projecting an optical marker on a floor to indicate a user where the turntable has to be placed.

It is advantageous if the optical marker indicates a distance, angle and/or orientation of the turntable relative to the second part. The distance, angle and/or orientation define a geometric relation between the turntable and the second part.

In an advantageous further aspect, the optical marker indicates a position of a point and/or a structure of the turntable, in particular a center point of rotation.

It is advantageous if the optical marker is a projected pattern, in particular a dot, a cross-pattern, a circle and/or an ellipse.

In an advantageous further aspect, the light emitter emits a light ray, light line, light cross and/or light cone.

It is advantageous if the light emitter comprises a diffuser, mask and/or means for moving the laser, in particular a collimator and/or a scanner, to generate the projected pattern.

In an advantageous further aspect, the light emitter is a laser or a light emitting diode (LED).

It is advantageous if the orientation of the fight emitter according to the second part is adjustable. Additionally or alternatively, the light emitter is detachable attached to the second part. Thus, the light emitter's direction of beam can be adjusted, in particular factory-made, relative to the second part.

In an advantageous further aspect, the 3D body scanner is designed in such a way that he can give a user an optical or acoustical feedback, when the turntable is placed relative to the second part with sufficient accuracy.

It is advantageous if the turntable comprises at least one optical detector, which is arranged in a target adjustment area of the turntable.

In an advantageous further aspect, the target adjustment area is a target adjustment point, target adjustment circle and/or target adjustment pattern.

It is advantageous if the optical detector detects the emitted light of the light emitter, when the turntable is placed relative to the second part with sufficient accuracy.

In an advantageous further aspect, the second part is a mast and/or comprises at least one depth sensor. The adjustment between the turntable and the at least one separate second part has to be done in such a manner that an object placed on the turntable is properly covered by the field of view of at least one depth sensor of the second part.

It is advantageous if the turntable is motor driven.

In an advantageous further aspect, both the turntable and the second part comprise a wireless interface to communicate with each other.

It is advantageous if the 3D body scanner comprises at least two second parts. In this case it is further advantageous if at least one of these second parts comprises at least one light emitter for projecting a first optical marker on the floor to indicate the user where the turntable has to be placed and/or for projecting a second optical marker on the floor to indicate the user where the other second part has to be placed.

To overcome the above mentioned problems and make a 3D body scanner convenient in use it is proposed to use in an advantageous way a projected pattern by a light ray, light cross, light cone or comparable to mark the target adjustment point(s) or circle(s) or pattern(s).

The projected pattern shall guide the user to place the first part, namely the turntable, of the 3D body scanner in an easy way in the proper distance and orientation to the second part, in particular the mast, without using meter sticks, templates or similar auxiliary tools.

In case that the 3D body scanner consists of multiple second parts, it is advantageous if the projected pattern may consist of multiple light rays, light crosses, light lines and/or comparable to indicate the positions of the other second parts and, if available the first part, too.

For increased convenience it may be further advantageous to place optical detectors at the target adjustment point or circle or pattern in order that the 3D scanner can give the user a, in particular optical or acoustical, feedback that a sufficient accuracy of placement is achieved.

It is advantageous if an optical marker from a projected pattern is illuminated and/or projected from the second part of a 3D body scanner to a dedicated spot region and/or shape on the first part, namely the turntable, of the 3D body scanner to indicate the relative distance between the first part and the second part.

It is advantageous if the projected light pattern is a dot, a cross-pattern, a circle, an ellipse and/or any other geometrical pattern to indicate where the center point of rotation and/or another point or structure of merit of the first part, namely the turntable, of the 3D body scanner has to be placed.

It is advantageous if the projected light pattern is a cross-pattern, an ellipse and/or any other geometrical pattern for indicating, if needed, in which orientation the first part, namely the turntable, of the 3D body scanner has to be placed in relation to the second part.

The position of multiple second parts and one first part, namely the turntable, of a 3D scanner can be advantageously indicated by multiple dot-, line-, cross-, circle-, ellipse and/or any other geometrical pattern from one or more light emitters mounted on one or more second parts of the 3D body scanner.

It is advantageous if the light emitter is a laser of whatever color with or without diffuser and/or mask to generate the pattern to be projected.

It is advantageous if the light source is an LED of whatever color with or without diffuser and/or mask to generate the pattern to be projected.

It is advantageous if the center point of rotation and/or another point or structure of merit of the first part, namely the turntable, of the 3D body scanner is one or a number of optical detectors which indicate that a sufficient accuracy of distance and/or orientation between the turntable and the second part is met. Advantageously, notice about reaching sufficient accuracy of distance and/or orientation between the turntable and the second part is given to the user in a, but not limited to, optical or acoustical way.

BRIEF DESCRIPTION OF THE DRAWINGS

Additional advantages of the invention are described in the following exemplary embodiments. The drawings show in.

DETAILED DESCRIPTION OF EXEMPLARY EMBODIMENTS OF THE INVENTION

Figure 1:
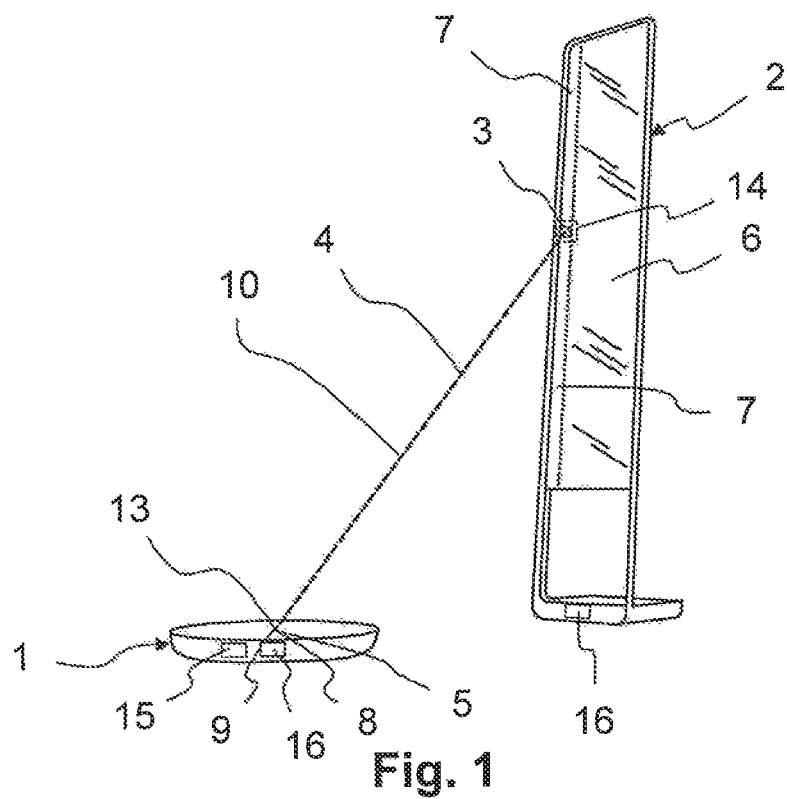
FIG. 1 a 3D body scanner for generating a 3D body model with a first exemplary embodiment of a projected pattern, FIG. 2 a 3D body scanner for generating a 3D body model with a second exemplary embodiment of a projected pattern and FIG. 3 a 3D body scanner for generating a 3D body model with a third exemplary embodiment of a projected pattern.
Figure 2:
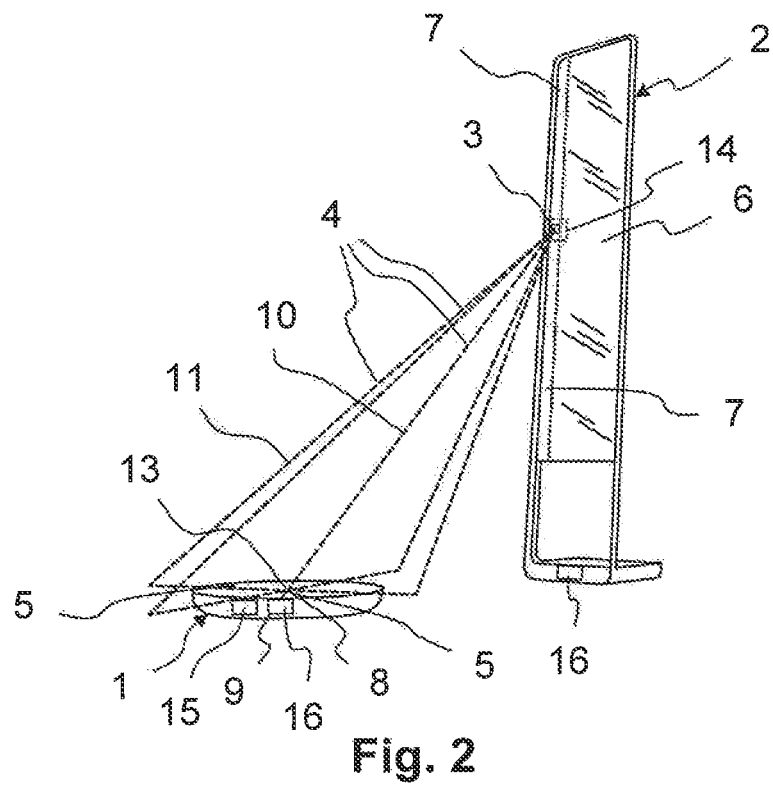
Figure 3:
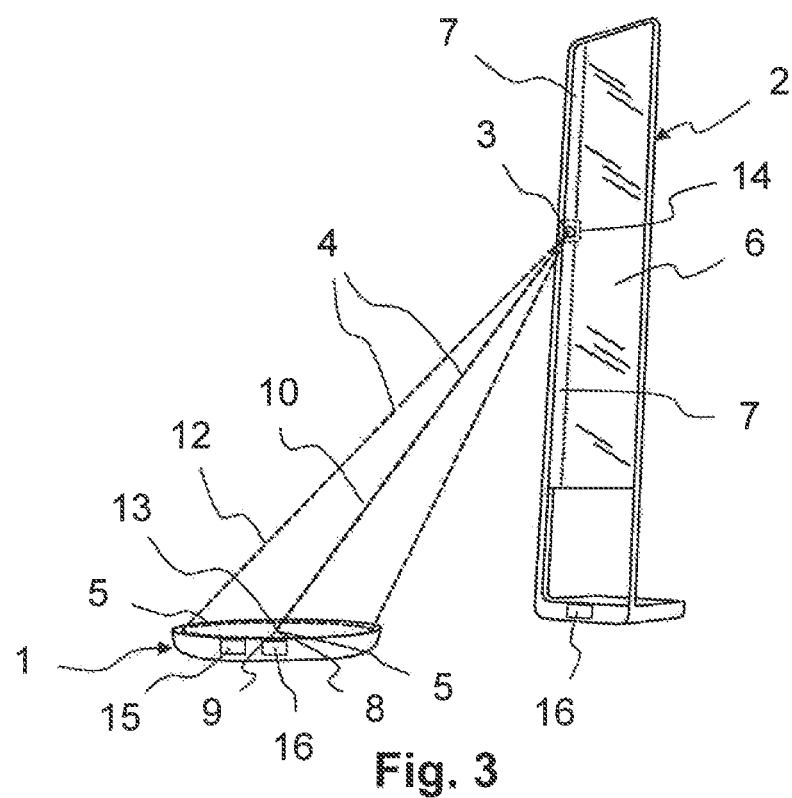

FIGS. 1, 2 and 3 show a 3D body scanner for generating a 3D body model. The 3D body scanner comprises a turntable 1 as a first part for turning around a body to be scanned. The turntable 1 is motor driven. Further, the 3D body scanner comprises a second part 2 for scanning the body. The second part 2 is formed as a mast that includes a mirror 6. For scanning the body placed on the turntable 1, the second part 2 comprises at least one depth sensor 7. In the embodiments shown in FIGS. 1, 2 and 3, the second part 2 comprises two depth sensors 7. Each of the two depth sensors 7 is placed at a different height with respect to each other.

The turntable 1 is separated from the second part 2. The 3D body scanner with separated turntable 1 and second part 2, in the particular embodiment a mast, is shown in different exemplary embodiments in FIGS. 1, 2 and 3. Because of the separation, the relative position between the turntable 1 and the second part 2 is not fixed, but rather is variable.

The turntable 1 has to be placed in a certain position with respect to the second part 2, in the particular embodiment with respect to the mast. Therefore, the second part 2 comprises a light emitter 3 for projecting an optical marker 8 on a floor to indicate to a user where the turntable 1 has to be placed with respect to the second part 2. The optical marker 8 indicates as a geometric relation, a distance, angle and/or orientation of the turntable 1 relative to the second part 2. The optical marker 8 indicates a position of a point and/or a structure of the turntable 1, in particular a center point of rotation 9 of the turntable 1. The optical marker 8 is a projected pattern, in particular a dot, a cross-pattern, a circle and/or an ellipse. In the FIGS. 1, 2 and 3 the turntable 1 is already aligned to the second part 2. Thus, a target adjustment area 5 of the turntable 1 is adjusted to or respectively superimposed by the optical marker 8.

For generating the optical marker 8, in particular the projected pattern, the light emitter 3 emits at least one light ray 4. The at least one light ray 4 can form a light line 10 as shown in FIGS. 1, 2 and 3. The light line 10 indicates the target position of the center point of rotation 9 of the turntable 1.

Additionally or alternatively, the light ray 4 can form a light cross 11, as shown in FIG. 2. The light cross 11 can additionally indicate the target orientation of the turntable 1 with respect to the second part 2.

Additionally or alternatively, the light ray 4 can form a light cone 12, as shown in FIG. 3. The light cone 12 can comply with the contour of the turntable 1.

For generating the optical marker 8, in particular the projected pattern, the light emitter 3 comprises a diffuser, a mask and/or a scanner, each of which being schematically represented in FIGS. 1, 2 and 3 and designated by the numeral 14. The diffuser 14, the mask 14 and/or the scanner 14 deviates the light ray 4 to create the projected pattern. The light emitter 3 is a laser or LED.

The 3D body scanner of FIGS. 1, 2 and 3 is designed in such a way that it can give a user a feedback, when the turntable 1 is placed relative to the second part 2 with sufficient accuracy, as shown in the figures. As schematically shown in FIGS. 1, 2 and 3, the feedback can be generated by a feedback device 15 and can be optical or acoustical. Therefore, the turntable 1 comprises at least one optical detector 13. The optical detector 13 is arranged in a target adjustment area 5 of the turntable 1. The target adjustment area 5 can comprise a target adjustment point, as shown in FIGS. 1, 2 and 3. Additionally or alternatively, the target adjustment area 5 can comprise a target adjustment pattern, in particular a cross, as shown in FIG. 2. Additionally or alternatively, the target adjustment area 5 can comprise a target adjustment circle, as shown in FIG. 3.

The optical detector 13 detects the emitted light of the light emitter 3, when the turntable 1 is placed relative to the second part 2 with sufficient accuracy. In this case, the turntable 1 is accurately positioned with respect to the second part 2 and the user gets a feedback signal. For this purpose and/or for controlling the motor of the turntable 1, as schematically shown in FIGS. 1, 2 and 3, both the turntable 1 and the second part 2 comprise a wireless interface 16 to communicate with each other. The wireless interface 16 can be a WLAN, WIFI, Zigbee and/or Bluetooth interface.

The disclosed invention enables a convenient way of adjusting two or multiple parts of a 3D body scanner in their positions of operation. The 3D body scanners consist, as mentioned before, of the first part 1, which is turning around the body to be scanned and in a defined distance and orientation with respect to the second part 2 covering that includes a number of depth sensors 7. Such a realization is shown as an example in FIGS. 1, 2 and 3. Alternative constructions consist of three or more second parts covering a number of depth sensors placed in a defined placement around the body (object) to be scanned.

3D body scanners are either very space consuming or they consist of two or more parts which have to be placed in a certain geometric relation (distance, angle, orientation) prior to usage. We propose a convenient way to perform this arrangement by projecting a pattern of visible light from an illumination source on the floor where the components of a 3D body scanner have to be placed. The illumination source can be a laser or a LED.

FIG. 1 shows a realization example with spot in center of turntable 1.

FIG. 2 shows a realization example with a cross pattern of light aimed to project on the center of turntable 1.

FIG. 3 shows a realization example with light in the form of a circle projected around turntable 1.

The 3D body scanner comprises:
the first part of the 3D scanner (e.g. turntable) carrying the body (object),
the second part of the 3D scanner (e.g. mast) containing the depth sensors 7,
the light emitter,
the light ray, light cross or light cone or comparable and/or
the target adjustment point or circle which may contain optical detectors 13.

LIST OF REFERENCE CHARACTERS 1. turntable
2. second part
3. light emitter
4. light ray
5. target adjustment area
6. mirror
7. depth sensor
8. optical marker
9. center point of rotation
10. light line
11. light cross
12. light cone
13. optical detector
14 diffuser, mask scanner
15 feedback device
16 wireless interface

The invention claimed is:

1. A three-dimensional (3D) human body scanner for generating a 3D human body model for fitness and body styling, comprising:
a first part that includes a scanner for scanning a human body;
a turntable that is spaced apart and physically disconnected from the first part and configured for carrying the human body that is to be scanned;
a light emitter carried by the first part and configured and disposed for projecting an optical marker,
wherein the optical marker indicates a position of the turntable to be placed relative to the first part, and
wherein the position is a distance from the first part;
an optical detector carried by the turntable in a target adjustment region of the turntable and configured for detecting the projected optical marker when the turntable is placed relative to the first part with a predetermined accuracy of the distance from the first part;
a feedback device configured to generate, based on the detection of the projected optical marker, to the user an optical or acoustical feedback when the turntable is placed relative to the first part with the predetermined accuracy of the distance from the first part; and
a wireless interface connecting the optical detector and the feedback device.

2. The 3D body scanner according to claim 1, wherein the turntable is configured to rotate about a center point of rotation, and wherein the optical marker is configured to indicate the center point of rotation.

3. The 3D body scanner according to claim 1, wherein the optical marker is a projected pattern.

4. The 3D body scanner according to claim 3, wherein the light emitter comprises a mask that is configured to generate the projected pattern.

5. The 3D body scanner according to claim 1, wherein the light emitter emits a light cone.

6. The 3D body scanner according to claim 1, wherein the light emitter is a laser or an LED a light emitting diode.

7. The 3D body scanner according to claim 1, wherein the target adjustment area is a target adjustment point, a target adjustment circle and/or a target adjustment pattern.

8. The 3D body scanner according to claim 1, wherein the first part is a mast.

9. The 3D body scanner according to claim 1, wherein the first part includes at least one depth sensor.

* * * * *